United States Patent
Kim et al.

Patent Number: 5,242,643
Date of Patent: Sep. 7, 1993

[54] BUBBLE COLUMN REACTOR WITH DISPERSING DEVICES

[75] Inventors: Sang D. Kim, Seoul; Yong K. Chang, Dajeon; Hee W. Ryu, Chunrabuk-do, all of Rep. of Korea

[73] Assignee: Korea Advanced Inst. of Science & Technology, Daejeon, Rep. of Korea

[21] Appl. No.: 915,913

[22] Filed: Jul. 17, 1992

[30] Foreign Application Priority Data

Aug. 29, 1991 [KR] Rep. of Korea ............... 1991-15018

[51] Int. Cl.⁵ .............................................. B01J 10/00
[52] U.S. Cl. .................................... 422/129; 422/231; 261/122.1
[58] Field of Search ................. 422/129, 99, 102, 255, 422/239, 231; 261/122.1

[56] References Cited
U.S. PATENT DOCUMENTS

| | | | |
|---|---|---|---|
| 2,461,649 | 2/1949 | Manning | 422/32 |
| 2,898,282 | 8/1959 | Flook, Jr. et al. | 261/122.1 |
| 4,105,725 | 8/1978 | Ross | 261/122.1 |
| 4,569,805 | 2/1986 | Hume et al. | 261/122.1 |
| 4,869,852 | 9/1989 | Goudy, Jr. et al. | 261/122.1 |
| 5,034,165 | 7/1991 | Willinger et al. | 261/122.1 |

Primary Examiner—Robert J. Warden
Assistant Examiner—Hien Tran
Attorney, Agent, or Firm—Morgan & Finnegan

[57] ABSTRACT

A bubble column reactor with at least one radial dispersing device to radially sparge a gas phase into a liquid phase in the bubble column. The reactor comprises four parts: bubble column body 4, radial dispersing device, a mounting plate, and a head plate. The radial dispersing device is employed to radially disperse the gas phase into the liquid phase. It has a porous wall and an outer threaded port 2 and is vertically installed in the bubble column 4. A mounting plate is employed to allow the dispersing devices 1 to be vertically installed. A head plate 8 is employed to cover the bubble column 4 and have ports 9 for sampling, exhaust gas and sensors. The bubble column reactor according to this invention provides advantages in that it can generate small bubble sizes, thus increase the residence time of the gas phase even under relatively high gas velocities and also relatively high viscosities of the liquid reactant, thereby improving the mass transfer performance of the reactor.

1 Claim, 4 Drawing Sheets

Fig. 2
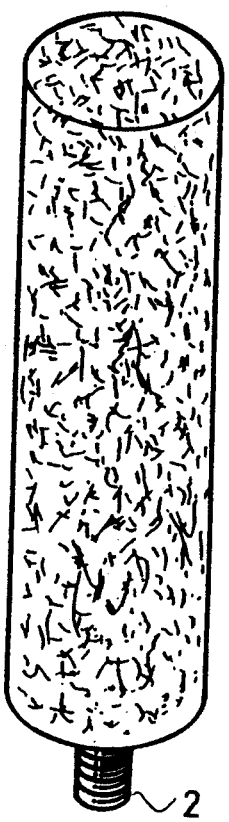
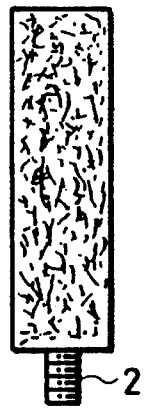
Fig. 3a
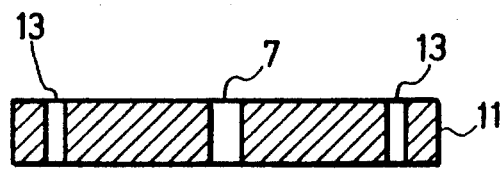
Fig. 3b

Fig. 4a
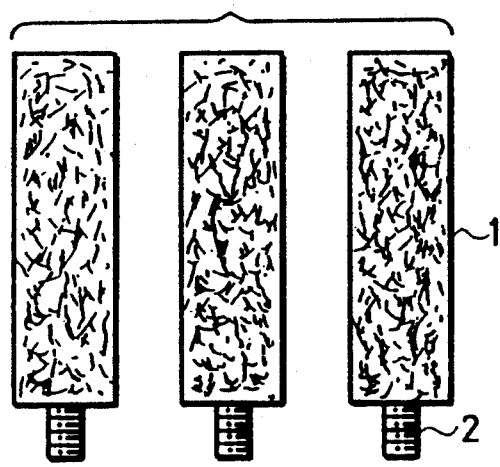
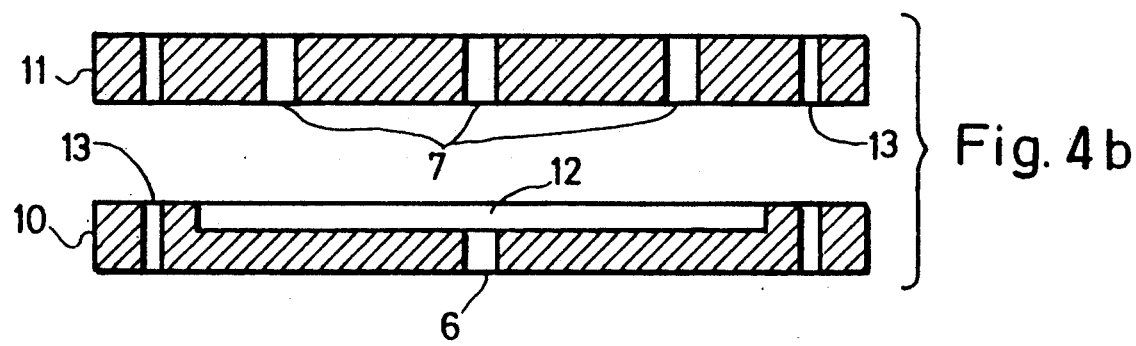
Fig. 4b

BUBBLE COLUMN REACTOR WITH DISPERSING DEVICES

BACKGROUND OF THE INVENTION

1. Field of the Invention

The present invention relates in general to a device for introducing gas into a liquid phase, and more particularly to a bubble column reactor having radial gas dispersing device vertically positioned in it. The radial dispersing devices are capable of improving the reactor performance in various reactions, particularly biological reactions involving gas and liquid phases or the like.

2. Description of the Prior Art

Recently, bubble column reactors are widely used in various industrial fields, such as petrochemical and bioprocess industries, and etc., as they efficiently provide advantages of relatively simple construction, relatively high mass and heat transfer rates, and a relatively cheap operational cost in comparison with other known types of reactors, for example, stirred tank reactors. Conventional bubble column reactors generally have a gas dispersing device comprising a porous plate, an orifice, a sintered plate, or the like, thereby allowing the gas to be vertically injected upward from the dispersing device and to be mixed with the liquid phase inside the bubble column.

However, conventional bubble column reactors have a disadvantage that the reactor performance decreases sharply with increasing gas velocity due to the formation of large gas bubbles. In addition, when viscosity of the liquid phase in the reactor is relatively high, the increases in bubble size causes a significant reduction in the interfacial area between the gas phase and the liquid phase, thereby resulting in a decreased mass transfer rate. Therefore, it has been required to develop a bubble column of improved performance in which the above disadvantages can be overcome.

SUMMARY OF THE INVENTION

The main objective of the present invention is to develop an effective bubble column reactor which can give high heat and mass transfer rates, and high reaction yields. In the present invention, a bubble column with radial dispersing devices was proposed in order to obtained high heat and mass transfer rates in various processes including fermentations. In detail, the bubble column reactor of this invention consists of a column, radial dispersing devices, a mounting plate and a head plate. Each radial dispersing device, which has a porous wall and is vertically installed in the bubble column, radially disperses the gas reactant into the liquid reactant. The mounting plate has gas inlet ports for the lower ports of the dispersing devices to fit in. The head plate of the column has a gas discharging port and sensor ports.

The radial dispersing device of this invention is made of sintered stainless steel, and has a cylindrical shape. Its inner space can act as an air chamber so that it needs no separate air chamber or needs only a small air chamber, unlike conventional plate type gas dispersing devices.

Unlike the conventional dispersing devices, the present dispersing device can be easily installed on the mounting plate with a screw and it can be easily replaced with different sizes without limitation of bubble column size. Additionally, in conventional bubble column reactors, the surface area of dispersing device is generally limited by the diameter of the reactor, but in the present bubble column reactor, it is possible to use a dispersing device of any required surface area irrespective of the diameter of the reactor. If a longer residence time of the gas phase is required in order to improve the mass transfer rate, radial dispersing devices of increased height and/or diameter should be used.

Particularly, the proposed type of radial dispersing device produces small bubble sizes, which allows a longer residence time of the gas phase even at the relatively high gas velocity and high viscosity of liquid phase.

BRIEF DESCRIPTIONS OF DRAWINGS

Detailed features and advantages of the present invention will be clearly understood from the following detailed descriptions given conjunction with the accompanying drawings:

FIG. 2 is a perspective view of the radial dispersing device of FIG. 1;

FIG. 3A is a view of the disassembled radial dispersing device in accordance with this invention;

FIG. 3B is a cross sectional view of a mounting plate for the radial dispersing device of FIG. 3A;

FIG. 4A is a view of a number of disassembled radial dispersing devices in accordance with this invention;

FIG. 4B is a cross sectional view of a double gas dispersing plate to be assembled with the radial dispersing devices of FIG. 4A; and In FIG. 5, mass transfer coefficients in a bubble column reactor in accordance with this invention are compared with those obtained in conventional bubble column and air-lift reactors.

DETAILED DESCRIPTION OF THE PREFERRED EMBODIMENTS

Figure 1:
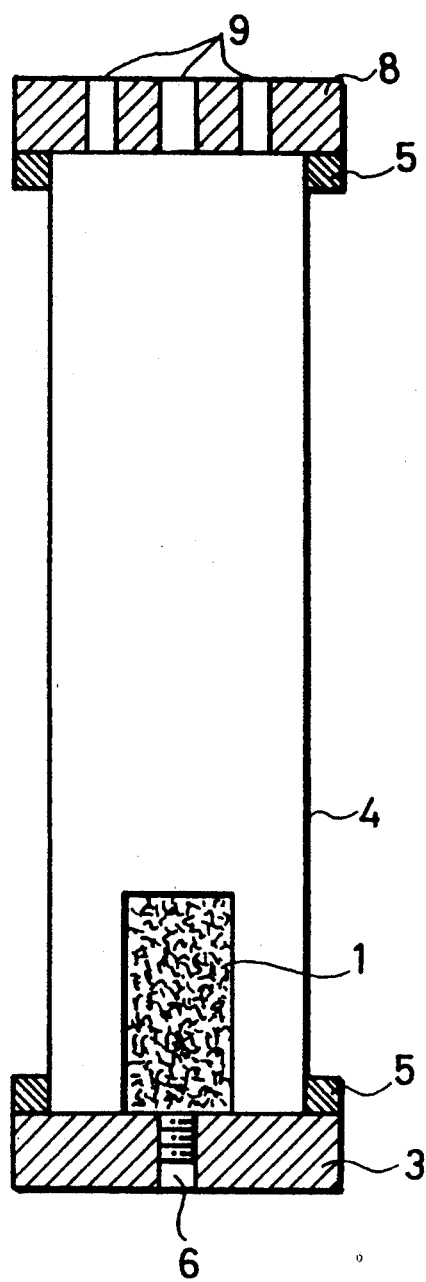
FIG. 1 is a longitudinal section of a bubble column reactor provided with a radial dispersing device in accordance with this invention.

Referring to FIG. 1 which is a longitudinal section view of an embodiment of a bubble column reactor with a radial dispersing device in accordance with this invention, the reactor is composed of the radial dispersing device 1, a mounting plate 3, and a bubble column 4. The device 1 is to radially disperse the gas phase into the liquid phase. The bubble column 4 is vertically installed on the mounting plate 3 which is provided with an inner threaded gas inlet port 6. The dispersing device 1 is made of a sintered stainless steel. It has a porous wall and an outer threaded port 2, as shown in FIG. 2 which is a perspective view of the radial dispersing device 1. The outer threaded port 2 fits into the inner threaded inlet port 6 of the plate 3.

The bubble column 4 is covered at the top thereof with a head plate 8 which has ports 9 such as a gas vent port, and several sensor, chemical addition and sampling ports. Flanger 5 are placed at each end of the column body. Each one is connected to the head plate and the mounting plate, respectively. The size of the bubble column 4 is variable depending upon the required capacity, but the ratio of the height to the diameter of the column is preferably designed greater than 10.

If the bubble column 4 has a relatively small diameter, it is provided with one dispersing device 1 installed at the center of the mounting plate 3 as shown in FIG. 1. The dispersing device 1 has an empty space which acts as an air chamber so that this reactor needs no auxiliary air chamber, which is essentially different from dispersing devices used in conventional bubble columns.

Turning to FIGS. 3A and 3B which show the radial dispersing device 1 and a mounting plate 11 in their disassembled state, according to this invention, the mounting plate 11 has an inner threaded inlet hole 7 with which the outer threaded inlet port 2 of the dispersing device 1 engages and a number of peripheral holes 13 for allowing setting screws (not shown) to be inserted therein. In the case of a bubble column reactor with a relatively larger diameter, it is preferable to have a number of radial dispersing devices 1 for the reactor, as shown in FIG. 4, while the reactor may be provided with only one dispersing device, as shown in FIG. 3.

The multiple radial dispersing devices 1 and a double gas dispersing plate according to this invention. The double gas dispersing plate comprises two plates, that is, a lower supporting plate 10 and an upper plate 11. The upper plate 11 is provided with a number of inner threaded inlet holes 7 arranged equidistanly to each other to be engaged with the outer threaded ports 2 of the dispersing devices 1. On the other hand, the lower supporting plate 10 has a depression 12. The gas phase is supplied to the dispersing device through this depression 12 when the plates 10 and 11 are assembled with each other. Additionally, the plates 10 and 11 have the peripheral holes 13 for allowing the setting screws to be inserted therein.

The present invention will be better understood with reference to the following examples; however these examples are intended to illustrate the invention. They must not to be construed to limit the scope of the present invention.

To evaluate the performance of the bubble column reactor according to the present invention, the performance of the invented reactor was compared with that of conventional bubble column reactors, in terms of mass transfer coefficient, gas holdup, bubble size, and interfacial area of gas-liquid phase. The bubble column 4 used in the embodiment of the present invention have a diameter of 120 mm and a height of 2.5 m. The radial dispersing device 1 has a mean pore size of 5 $\mu$m, a length of 150 mm, and a diameter of 38.1 mm. The surface area of the radial dispersing device 1 used in accordance with the present invention was 0.018 $m^2$ which is about 1.6 times the surface area (0.0113 $m^2$) of plate type dispersing device in a conventional bubble column reactor with the same column diameter. The lower inlet port 2 of the dispersing device has a diameter of 6.3 mm. These dimensions may be varied, depending on the application of the reactor.

EXAMPLE 1

Comparison with conventional bubble column and airlift reactors

Figure 5:
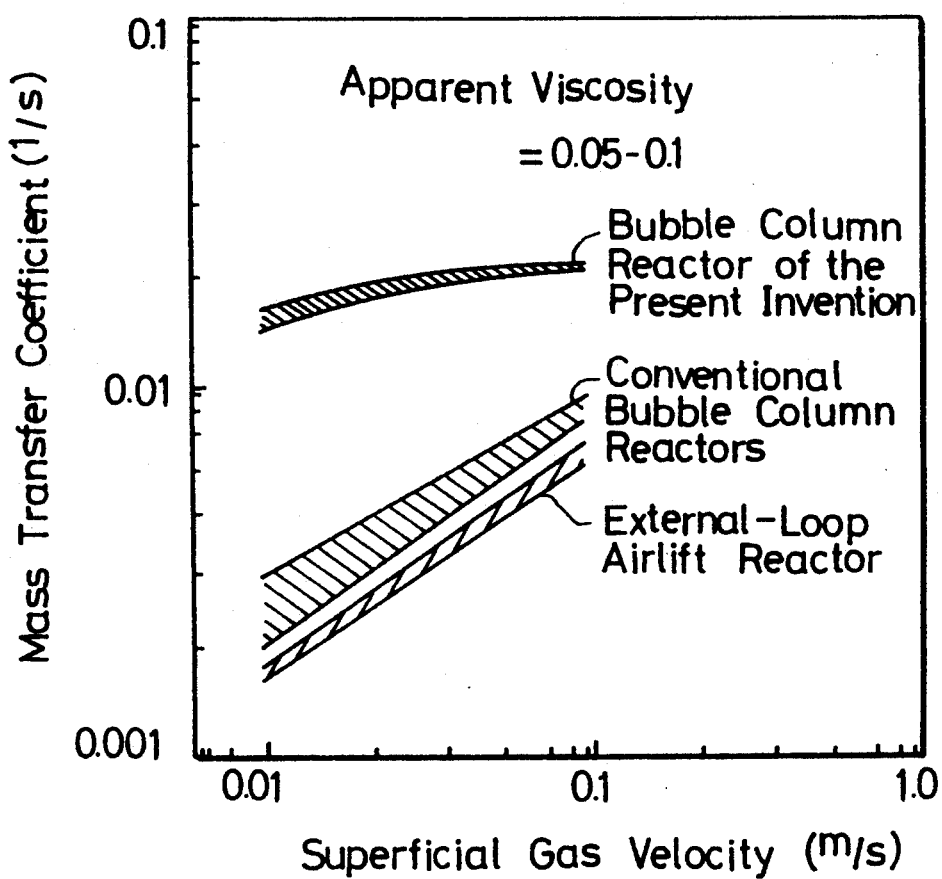

CMC (carboxymethyl cellulose) solutions which simulate characteristics of a non-Newtonian fluid such as mycelium fermentation broths were used in order to test the performance of the invented reactor. The gas holdup of bubble column reactor with the radial dispersing device 1 according to the present invention was 1.5 to 3 times higher than that of conventional bubble column reactors. Also, as is shown in FIG. 5, the mass transfer performance of the invented reactor is 1.5 to 3 times better than that of conventional reactors under the same conditions.

With the invented reactor, the bubble size was very small under most operating conditions, giving a large interfacial areas and thus increased mass transfer rate.

EXAMPLE 2

Application for enzyme production

Lipase was produced from *Rhizopus oligosporus* which is a filamentous mycelium in the invented reactor. The present reactor provides high mass transfer coefficient even highly viscous mycelial fermentation broths with high cell, allowing sufficient amount of oxygen required for the cells to be supplied. Thus, high productivities of lipase from *Rhizopus oligosporus* without limitation of oxygen transfer in the invented reactor was obtained.

As a result, the bubble column reactor with the radial dispersing device according to this invention can be effectively used in the fermentations of shear sensitive cells such as mycelial fungi, animal cells and plant cells. In addition, the reactor provides high mass transfer rates even with viscous solutions such as in the production of biopolymers using microorganism or as in operating with a slurry solution. Thus the invented reactor is appropriate for the fermentation of aerobic microorganisms which require large amount of oxygen. Moreover, the reactor is effectively applied to general chemical reactions such as adsorption reactions in which a substantially long residence time of the gas phase is required.

Although the preferred embodiments of the present invention have been disclosed for illustrative purpose, those who are skilled in the art will appreciate that various modifications, additions and substitutions are possible, without departing from the scope and spirit of the invention as disclosed in the accompanying claims.

What is claimed is:

1. A bubble column reactor comprising:
   a bubble column having a height to diameter ratio greater than 10;
   at least one dispersing device for dispersing at least oxygen into a liquid phase, said dispersing device having a porous wall, and an outer threaded port, a surface area of said dispersing device being more than 1.6 times greater than a cross-sectional area of the bubble column and said dispersing device being vertically installed in the bubble column, said porous wall having pores formed therein to provide a dispersing device that is oxygen permeable;
   a mounting plate for allowing said dispersing device to be vertically mounted thereon, said mounting plate having a gas inlet port being connected to said outer threaded port of said dispersing device; and
   a head plate for covering the bubble column, said head plate having a gas discharging port and a number of ports for various sensors, liquid reactant supply and product discharge.

* * * * *